US008309556B2

(12) United States Patent
Weill et al.

(10) Patent No.: US 8,309,556 B2
(45) Date of Patent: Nov. 13, 2012

(54) USE OF COMPOUNDS DERIVED FROM PYRIMIDINETRIONE AS ACETYL CHOLINESTERASE INHIBITORS, COMPOSITIONS CONTAINING SAID DERIVATIVES, AND THE USES THEREOF

(75) Inventors: Mylene Weill, Montpellier (FR); Philippe Fort, Castelnau le Lez (FR); Jean-Paul Leonetti, Castelnau le Lez (FR)

(73) Assignees: Centre National de la Recherche Scientifique, Paris (FR); Universite de Montpellier 2, Montpellier (FR)

( * ) Notice: Subject to any disclaimer, the term of this patent is extended or adjusted under 35 U.S.C. 154(b) by 862 days.

(21) Appl. No.: 11/816,032

(22) PCT Filed: Feb. 10, 2006

(86) PCT No.: PCT/FR2006/000307
§ 371 (c)(1),
(2), (4) Date: Nov. 27, 2007

(87) PCT Pub. No.: WO2006/097588
PCT Pub. Date: Sep. 21, 2006

(65) Prior Publication Data
US 2008/0269252 A1    Oct. 30, 2008

(30) Foreign Application Priority Data
Feb. 10, 2005  (FR) ..................... 05 01328

(51) Int. Cl.
*A01N 43/54* (2006.01)
*C07D 239/42* (2006.01)
*C07D 401/04* (2006.01)

(52) U.S. Cl. ....................................... 514/256; 544/298
(58) Field of Classification Search ................ 544/299; 514/298, 256
See application file for complete search history.

(56) References Cited

U.S. PATENT DOCUMENTS
5,162,327 A * 11/1992 Kratt et al. ............... 514/270

FOREIGN PATENT DOCUMENTS
FR        0 382 112           8/1990
FR        0 455 300          11/1991
WO    WO 03074497 A1  *  9/2003

OTHER PUBLICATIONS
Patini et al. Bioisosterism: A Rational Approach in Drug Design, Chem. Rev. 1996, 96 (8), 3147-3176.*
Shiro (1, 3-Dimethylbarbituric acid as an aldehydes reagent, Berichte der Deutschen Chemischen Gesellschaft [Abteilung] B; Abhandlungen (1993), 66B 139-43), STN Abstract.*
Patini et al Bioisosterism: A rational approach in drug design, Chem. Rev. 1996, vol. 96, pp. 3147-3176.*
Yajima et al "Proteome-level differences between auxinic-succeptible and resistant wild mustard (*Sinapsis arvensis* L.", J. Agric. Food Chem., 2004, vol. 52, pp. 5063-5070.*

* cited by examiner

*Primary Examiner* — Brandon Fetterolf
*Assistant Examiner* — Jean Cornet
(74) *Attorney, Agent, or Firm* — Oblon, Spivak, McClelland, Maier & Neustadt, L.L.P.

(57) ABSTRACT

The invention relates to the use of compounds derived from pyrimidinetrione of general formula (I) as acetyl cholinesterase (AChE) inhibitors. The invention also relates to the use of said compounds as insecticides, and to compositions containing the same.

2 Claims, No Drawings

USE OF COMPOUNDS DERIVED FROM PYRIMIDINETRIONE AS ACETYL CHOLINESTERASE INHIBITORS, COMPOSITIONS CONTAINING SAID DERIVATIVES, AND THE USES THEREOF

The present invention relates to the use of compounds derived from pyrimidinetrione of general formula (I) as defined below as acetylcholinesterase (AChE) inhibitors, to their use as insecticides and to the compositions comprising these derivatives.

Intensive control of insects is practiced in many parts of the world by large-scale treatment using insecticides, which has gradually resulted in the emergence of populations of insects resistant to the treatments.

The emergence of populations of insects resistant to the commonly used insecticides represents an important public health problem insofar as some insects are the vectors for the transmission of diseases to man, such as, for example, the mosquitoes which transmit malaria (*Anopheles gambiae*), yellow fever and dengue fever (*Aedes aegypti*) or viral encephalopathies (*Culex tritaeniorhynchus* and *Culex pipiens*).

Mention may be made, among the most widely used insecticides, of organophosphorus compounds and carbamates. The target of these two main families of insecticides is acetylcholinesterase (AChE), an essential enzyme which hydrolyzes acetylcholine in the cholinergic synapses. Inhibition of AChE prevents deactivation of the synaptic signal, thus resulting in a loss in control of cholinergic transmission.

Among the mechanisms of resistance, the selection of mutations which render AChE insensitive to organophosphorus and carbamate insecticides has been observed in numerous cases (Anazawa Y., Insect Biochem. Mol. Biol., 2003, 33(5), 509-514; Fallang A., Pest. Manag. Sci., 2004, 60(12), 1163-1170; Li F., Insect Biochem. Mol. Biol., 2004, 34(4), 397-405; Menozzi P., BMC Evol. Biol., 2004, 4(1), 4; Nabeshima T., Biochem. Biophys. Res. Commun., 2004, 313 (3), 794-801; Vontas J G., Insect Mol. Biol. 2002, 11(4), 329-336; Walsh S B., Biochem. J., 2001, 359 (Pt I), 175-181).

The inventors have thus previously identified in the Culicidae (mosquitoes) the gene encoding AChE, the target of the organophosphorus compounds and carbamates. Furthermore, one and the same mutation (glycine to serine at position 119 according to the Torpedo AChE nomenclature) has been encountered in all the populations of several species of mosquitoes which exhibit a high level of resistance to organophosphorus compounds and to carbamates and in particular in *Culex pipiens*, *Anopheles gambiae* and *Anopheles albimanus*, namely the main vectors of yellow fever, malaria and viral encephalopathies (Weill et al., Insect Molecular Biology, 2004, 13(1), 1-7; Weill et al., Nature, 2003, 423, 136-137).

In view of the above, it is thus apparent that the development of novel strategies for combating insects represents a crucial health and economic challenge.

Many researchers have attempted to diversify the biological target in order to circumvent these established resistances. However, while such a diversification is desirable in the long term, it will not prevent the appearance of resistant populations and will require a major effort in order to achieve the level of knowledge already acquired with regard to the targets currently targeted.

Another possibility consists in looking for molecules which are effective with regard to the resistant forms of the targets already authenticated. The major advantage of this approach is the lower probability of the targets accepting an additional mutation without resulting in a deleterious effect due to a reduction in their activity.

The inventors have chosen this second approach and have set themselves the aim of finding novel insecticides capable of killing the populations of insects which have developed resistance to conventional insecticides.

Thus, the inventors have identified a family of compounds capable of inhibiting AChE and preferably of acting on AChE insensitive to organophosphorus compounds and to carbamates. Such compounds thus have insecticidal properties and are capable of acting in particular preferably on populations of insects which have developed resistance to conventional insecticides.

Thus, the compounds according to the present invention can advantageously be used to control the growth of populations resistant to organosphosphorus compounds and to carbamates. Furthermore, in view of the reduction of 40% in the specific activity occasioned by the first mutation, the probability of AChE retaining a sufficient activity following an additional mutation is not very great. The use of the insecticidal compounds of this type would thus make it possible to prevent the spreading of the species currently resistant while minimizing the risks of appearance of fresh resistance to these novel compounds.

Furthermore, the structure of these compounds makes it possible, for example by combinatorial chemistry, to obtain a large number of alternative forms of these compounds, which should make it possible to rapidly adapt them to the emergence of possible subsequent resistances. These molecules are also relatively unstable in an aqueous medium, which is an advantage in the protection of the environment (low persistence).

According to a first aspect, a subject matter of the invention is the use of at least one compound derived from pyrimidinetrione as AChE inhibitor, said compound corresponding to the following general formula (I):

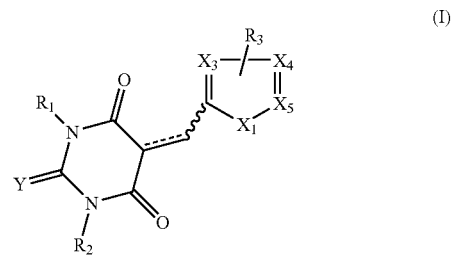

in which:

----- represents a bond which can be a single bond or a double bond;

$R_1$ represents a group chosen from a hydrogen atom and a saturated or unsaturated, linear, branched or cyclic, $C_1$-$C_6$ alkyl group optionally substituted by a hydroxyl group or a halogen atom;

$R_2$ represents a group chosen from an optionally substituted aryl group and a saturated or unsaturated, linear, branched or cyclic, $C_1$-$C_4$ alkyl group optionally substituted by one or more groups chosen from halogen atoms, hydroxyl groups, heterocycles comprising 1 to 5 carbon atoms and 1 to 5 heteroatoms, such as oxygen, sulfur and nitrogen;

$R_3$ can be in a 3, 4 or 5 position of the ring and represents a group chosen from a hydrogen atom and a saturated or unsaturated, linear, branched or cyclic, $C_1$-$C_4$ alkyl group optionally substituted by a hydroxyl group or a halogen atom;

$X_1$ represents an atom chosen from sulfur, nitrogen and oxygen;

$X_3$, $X_4$ and $X_5$, which are identical or different, are chosen from a carbon atom and a nitrogen atom, at most two atoms from $X_3$, $X_4$ and $X_5$ being nitrogen atoms; and Y represents an atom chosen from oxygen and sulfur.

When $R_2$ is a substituted aryl group, it is substituted by a $C_1$-$C_4$ alkyl or alkoxy group, such as, for example, a methyl, ethyl, n-propyl, isopropyl, n-butyl, tert-butyl or isobutyl group or a methoxy, ethoxy, isopropoxy or butoxy group. It can also be substituted by a hydroxyl group or a halogen atom chosen from chlorine, bromine, iodine and fluorine, in particular chlorine. Furthermore, the substitution of the aryl group can take place in the ortho, meta or para position and preferably in the meta or para position.

Mention may in particular be made, among the

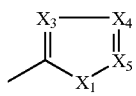

rings which can be used in the above formula (I), of:

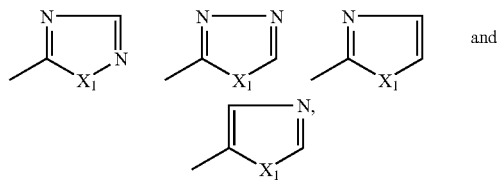

and $X_1$ having the same definition as above.

Patent application DE 3903404 discloses pyrimidinetrione derivatives used as insecticides and anthelmintics in particular.

European patent EP 0 455 300 discloses barbituric acid derivatives and their use as insecticides; the targets targeted being other than mosquitoes.

However, the compounds described in these two documents are different from those corresponding to the general formula (I) as defined above. In addition, none of the documents of the prior art suggests or mentions an inhibitory activity for AChE, in particular an inhibitory activity for an AChE form resistant to organophosphorus and carbamate insecticides.

According to a preferred form of the invention, when $R_1$, represents a $C_1$-$C_6$ alkyl group, the latter is preferably a $C_1$-$C_4$ alkyl group and more preferably a methyl group. Thus, mention may in particular be made, among the preferred compounds according to the invention, of the compounds in which $R_1$ is chosen from a hydrogen atom and a methyl group.

According to another preferred form of the invention, $R_2$ represents an aryl group optionally substituted by a group chosen from a $C_1$-$C_4$ alkyl and a halogen atom and advantageously a phenyl optionally substituted by a group chosen from a $C_1$-$C_4$ alkyl and a halogen atom.

Mention may in particular be made, among the preferred compounds according to the invention, of the compounds in which $R_2$ is chosen from a methyl, an allyl, a furyl group optionally substituted by a methyl, a butyl, an unsubstituted phenyl, a phenyl substituted by a methyl group in the meta position, a phenyl substituted by a methyl group in the para position, a phenyl disubstituted in the meta and para position by a methyl, a phenyl substituted by an ethyl in the para position, a phenyl substituted by a methoxy group in the meta position, a phenyl substituted by a methoxy group in the para position, a phenyl substituted by an ethoxy in the para position, a phenyl substituted by an isopropyl in the para position, a phenyl substituted by a chlorine atom in the para position, a phenyl substituted by a bromine atom in the para position, a phenyl substituted by a fluorine atom in the para position. In the preferred compounds according to the invention, Y advantageously represents an oxygen atom.

According to a preferred form of the invention, $X_1$ is chosen from oxygen and sulfur.

Advantageously, the compounds according to the invention are compounds in which $X_3$, $X_4$ and $X_5$ are identical and all represent a carbon atom.

Mention may in particular be made, among the preferred compounds according to the invention, of the compounds in which $R_3$ is chosen from a hydrogen atom and a methyl group. Furthermore, $R_3$ is advantageously in the 5 position of the furan, thiophene or pyrrole ring.

Mention may in particular be made, among the compounds of formula (I) above, of the following preferred compounds listed in table I:

TABLE I

| Compounds | Names |
|---|---|
| (1) | 5-[(5-methyl-2-furyl)methylene]-1-phenyl-2,4,6(1H,3H,5H)-pyrimidinetrione |
| (2) | 1-(3-methylphenyl)-5-[(5-methyl-2-thienyl)methylene]-2,4,6(1H,3H,5H)-pyrimidinetrione |
| (3) | 1-(3-methoxyphenyl)-5-[(5-methyl-2-thienyl)methylene]-2,4,6(1H,3H,5H)-pyrimidinetrione |
| (4) | 1,3-dimethyl-5-[(5-methyl-2-furyl)methylene]-2,4,6(1H,3H,5H)-pyrimidinetrione |
| (5) | 1-(4-methoxyphenyl)-5-[(5-methyl-2-furyl)methylene]-2,4,6(1H,3H,5H)-pyrimidinetrione |
| (6) | 1-(4-chlorophenyl)-5-[(5-methyl-2-furyl)methylene]-2,4,6(1H,3H,5H)-pyrimidinetrione |
| (7) | 1-(4-isopropylphenyl)-5-[(5-methyl-2-furyl)methylene]-2,4,6(1H,3H,5H)-pyrimidinetrione |
| (8) | 1-allyl-5-[(5-methyl-2-furyl)methylene]-2-thioxodihydro-4,6(1H,5H)-pyrimidinetrione |
| (9) | 5-(2-furylmethylene)-1-phenyl-2,4,6(1H,3H,5H)-pyrimidinetrione |
| (10) | 5-(2-furylmethylene)-1,3-dimethyl-2,4,6(1H,3H,5H)-pyrimidinetrione |
| (11) | 5-[(5-methyl-2-furyl)methylene]-1-(4-methylphenyl)-2,4,6(1H,3H,5H)-pyrimidinetrione |
| (12) | 1-(3-methoxyphenyl)-5-[(5-methyl-2-furyl)methylene]-2,4,6(1H,3H,5H)-pyrimidinetrione |
| (13) | 1-(4-ethoxyphenyl)-5-[(5-methyl-2-furyl)methylene]-2,4,6(1H,3H,5H)-pyrimidinetrione |
| (14) | 1-(4-bromophenyl)-5-[(5-methyl-2-thienyl)methylene]-2,4,6(1H,3H,5H)-pyrimidinetrione |
| (15) | 1-(4-chlorophenyl)-5-[(5-methyl-2-thienyl)methylene]-2,4,6(1H,3H,5H)-pyrimidinetrione |
| (16) | 1-(4-fluorophenyl)-5-[(5-methyl-2-thienyl)methylene]-2,4,6(1H,3H,5H)-pyrimidinetrione |
| (17) | 1-(3,4-dimethylphenyl)-5-[(5-methyl-2-furyl)methylene]-2,4,6(1H,3H,5H)-pyrimidinetrione |
| (18) | 1-(2-furylmethyl)-5-[(5-methyl-2-furyl)methylene]-2,4,6(1H,3H,5H)-pyrimidinetrione |
| (19) | 1-(4-ethylphenyl)-5-[(5-methyl-2-furyl)methylene]-2,4,6(1H,3H,5H)-pyrimidinetrione |
| (20) | 1-butyl-5-[(5-methyl-2-thienyl)methylene]-2,4,6(1H,3H,5H)-pyrimidinetrione |

The preferred compounds which are cited in the above table are known as such and are described in particular in the following publications: Vvedenskii, V M., Khimiya Geterotsiklicheskikh Soedinenii, 1969, 6, 1092-1095; El-Badawi, M., Journal of Science, 1990, 14(2), 581-600. However, their insecticidal activity has never been demonstrated in the prior art.

Due to the inhibitory activity for AChE exhibited by the compounds derived from pyrimidinetrione of general formula (I) according to the present invention, these compounds can also be used in the preparation of a medicament intended to treat disorders associated with dysfunctioning of AChE and in particular neurodegenerative diseases, such as Alzheimer's disease. Specifically, the compounds of the invention have shown an inhibitory activity with regard to recombinant human AChE.

According to a second aspect, the subject matter of the invention is the use of at least one compound of general formula (I) as insecticide.

All the preferred compounds of general formula (I) as defined above can be used as insecticide.

The compounds of general formula (I) can be used to control the growth of populations of various types of insects, in particular of the genus *Aedes, Culiseta, Ochlerotatus, Uranoteania, Anopheles* or *Culex*, preferably of the genus *Anopheles* or *Culex*, in particular for the deinfestation of inhabited regions or more generally of regions where a human activity is carried out, such as agricultural regions, for example.

Mention may in particular be made, among the insects of the genus *Anopheles* or *Culex*, of the species chosen from *Culex deserticola, Culex hortensis, Culex pipiens pipiens, Culex pipiens, Culex pipiens quinquefasciatus, Culex pipiens molestus, Culex tigripes, Anopheles albimanus, Anopheles arabiensis, Anopheles gambiae, Anopheles hyrcanus, Anopheles subpicus* and *Anopheles sundaicus*.

According to a preferred form of the invention, the compounds of general formula (I) are used on populations of insects which have developed resistance to organophosphorus insecticides or to carbamates. This is because the inventors have found, surprisingly, that, while the activity of these compounds with regard to populations of insects sensitive to carbamates and to organophosphorus compounds is comparable with or even inferior to that of these insecticides which have been known for a long time, these compounds are much more active with regard to the populations of insects resistant to these conventional insecticides.

According to another preferred form, the compounds of general formula (I) according to the present invention are used in combination with at least one other conventional insecticide, thus making it possible to treat regions in which populations of insects more or less sensitive or resistant to the various conventional insecticides coexist. The combination of at least one compound of general formula (I) and of at least one insecticide chosen from carbamates and organophosphorus compounds constitutes another subject matter of the invention.

Application can be carried out conventionally, for example by sprinkling, spraying, diffusion, painting, dry treatment, wet treatment, dipping, suspending or crusting.

Due to the insecticidal properties exhibited by the pyrimidinetrione derivatives of general formula (I) according to the present invention, these compounds can also be used as comparative product in carrying out evaluation tests on insecticidal properties.

For practical operating reasons, the compounds of general formula (I) according to the present invention can be provided in the form of compositions.

Thus it is that, according to a third aspect, a subject matter of the invention is an insecticidal composition comprising at least one compound of general formula (I) in combination with a carrier appropriate for the use of the composition as insecticide.

In the composition according to the present invention, the active compounds are mixed with a solid carrier or are dissolved or dispersed in a liquid carrier. The compounds can also be used in combination with additional substances, such as emulsifiers, wetting agents, dispersing agents and stabilizers.

The compounds derived from pyrimidinetrione of general formula (I) and the compositions comprising them according to the present invention can be incorporated in conventional formulations, such as solutions, emulsions, suspensions, powders, foams, pastes, granules, aerosols, and the like, said formulations being prepared by conventional techniques well known to a person skilled in the art.

According to a preferred form, the insecticidal composition of the invention additionally comprises at least one other compound possessing an insecticidal activity and in particular an insecticidal compound chosen from organophosphorus compounds and carbamates.

Furthermore, the insecticidal composition can additionally comprise one or more other active substances, such as, for example, acaricides, fungicides, bactericides, manures, fertilizers, and the like.

The compositions according to the invention are effective against populations of insects of normal sensitivity or which are resistant to organophosphorus compounds or to carbamates, as well as all the developmental stages of insects. This is because, the acetylcholinesterase activity being required for correct transmission of the nervous influx, the compounds of the invention are inhibitors of AChE (wild-type or G119S-mutated) and are thus active as soon as the activity of the enzyme is required (sensitive larvae die from the eclosion, thus at the L1 developmental stage).

The application forms as described above relating to the use of pyrimidinetrione derivatives of general formula (I) as insecticides (sprinkling, spraying, and the like) are also applicable to the compositions comprising them, whether or not the latter additionally comprise other active substances or auxiliaries.

Finally, according to a final aspect, a subject matter of the invention is an insecticidal kit comprising at least one composition as described above in combination with a diffusion means which makes possible the application of said composition over a district composed of one or more agricultural and/or residential and/or forestry and/or marshy and/or steppe and/or savannah regions.

The present invention will be better understood with the help of the remainder of the description which will follow, which refers to examples demonstrating the property inhibiting AChE of several compounds derived from pyrimidinetrione of general formula (I) according to the invention and demonstrating the insecticidal property of these compounds and to the preparation of a composition comprising these compounds.

EXAMPLE 1

Inhibitory property of the ache activity of the Compounds of General Formula (I)

The compounds derived from pyrimidinetrione of general formula (I) according to the invention which are combined in table II below were tested for their inhibitory activity on AChE. These compounds are all sold by Chembridge Corporation (San Diego, USA).

TABLE II

| Compounds | Names |
|---|---|
| (1) | 5-[(5-methyl-2-furyl)methylene]-1-phenyl-2,4,6(1H,3H,5H)-pyrimidinetrione |
| (2) | 1-(3-methylphenyl)-5-[(5-methyl-2-thienyl)methylene]-2,4,6(1H,3H,5H)-pyrimidinetrione |
| (3) | 1-(3-methoxyphenyl)-5-[(5-methyl-2-thienyl)methylene]-2,4,6(1H,3H,5H)-pyrimidinetrione |
| (4) | 1,3-dimethyl-5-[(5-methyl-2-furyl)methylene]-2,4,6(1H,3H,5H)-pyrimidinetrione |
| (5) | 1-(4-methoxyphenyl)-5-[(5-methyl-2-furyl)methylene]-2,4,6(1H,3H,5H)-pyrimidinetrione |
| (6) | 1-(4-chlorophenyl)-5-[(5-methyl-2-furyl)methylene]-2,4,6(1H,3H,5H)-pyrimidinetrione |
| (7) | 1-(4-isopropylphenyl)-5-[(5-methyl-2-furyl)methylene]-2,4,6(1H,3H,5H)-pyrimidinetrione |
| (8) | 1-allyl-5-[(5-methyl-2-furyl)methylene]-2-thioxodihydro-4,6(1H,5H)-pyrimidinetrione |
| (9) | 5-(2-furylmethylene)-1-phenyl-2,4,6(1H,3H,5H)-pyrimidinetrione |
| (10) | 5-(2-furylmethylene)-1,3-dimethyl-2,4,6(1H,3H,5H)-pyrimidinetrione |
| (11) | 5-[(5-methyl-2-furyl)methylene]-1-(4-methylphenyl)-2,4,6(1H,3H,5H)-pyrimidinetrione |
| (12) | 1-(3-methoxyphenyl)-5-[(5-methyl-2-furyl)methylene]-2,4,6(1H,3H,5H)-pyrimidinetrione |
| (13) | 1-(4-ethoxyphenyl)-5-[(5-methyl-2-furyl)methylene]-2,4,6(1H,3H,5H)-pyrimidinetrione |
| (14) | 1-(4-bromophenyl)-5-[(5-methyl-2-thienyl)methylene]-2,4,6(1H,3H,5H)-pyrimidinetrione |
| (15) | 1-(4-chlorophenyl)-5-[(5-methyl-2-thienyl)methylene]-2,4,6(1H,3H,5H)-pyrimidinetrione |
| (16) | 1-(4-fluorophenyl)-5-[(5-methyl-2-thienyl)methylene]-2,4,6(1H,3H,5H)-pyrimidinetrione |
| (17) | 1-(3,4-dimethylphenyl)-5-[(5-methyl-2-furyl)methylene]-2,4,6(1H,3H,5H)-pyrimidinetrione |
| (18) | 1-(2-furylmethyl)-5-[(5-methyl-2-furyl)methylene]-2,4,6(1H,3H,5H)-pyrimidinetrione |
| (19) | 1-(4-ethylphenyl)-5-[(5-methyl-2-furyl)methylene]-2,4,6(1H,3H,5H)-pyrimidinetrione |
| (20) | 1-butyl-5-[(5-methyl-2-thienyl)methylene]-2,4,6(1H,3H,5H)-pyrimidinetrione |

The inhibitory properties of the compounds of the preceding table I are tested with regard to the AChE activity by either using a normal or G119S-mutated recombinant AChE or using extracts of larvae of mosquitoes which are sensitive (carrying normal AChE) or resistant (carrying G119S-mutated AChE) to organophosphorus compounds and carbamates.

The AChE activity is measured using the method described by Bourguet et al., Pest Biochem. Physiol., 1996, 55, 122-128, and which refers to the spectroscopic method described by Ellman G. L. et al. (Biochem. Pharmacol., 1961, 7, 88-95) using acetylthiocholine as substrate.

1) Property of Inhibiting the Activity of a Recombinant AChE

The inhibitory properties of the compounds according to the invention with regard to the activity of a G119S-mutated or normal recombinant *Culex pipiens* AChE1 are tested according to protocol described by Weill et al., Nature, 2003, 423, 136-137.

Each compound according to the invention is tested at different concentrations on lysates of Drosophile S2 cells transfected with an empty expression vector or an expression vector expressing normal or mutated AChE1. After expression, the cells are centrifuged for 15 minutes at 14 000 rpm and are subsequently lysed in a 0.25 M phosphate buffer comprising 1% Triton X100.

100 µl of supernatant originating from the centrifuging of the cell lysates at 10 000 rpm for 3 minutes are incubated for 15 minutes with 10 µl of each compound according to the invention at various concentrations. The activity of known inhibitors of AChE, namely tacrine and propoxur (insecticide of the carbamate type), is also tested in parallel with regard to the AChE activity (tacrine and propoxur are available commercially from ICN Biomedical and Bayer AG respectively).

For each compound tested, the concentration resulting in 50% inhibition of the AChE activity is determined ($IC_{50}$ in µM). The effectiveness of the various compounds with regard to the mutated AChE activity, relative to that of the normal AChE, is estimated by the sensitive/insensitive ratio.

The results obtained ($IC_{50}$ in µM and sensitive/insensitive ratio) are summarized below in table III.

TABLE III

| Compounds | Mutated AChE1 (insensitive protein) | Normal AChE1 (sensitive protein) | Sensitive/ insensitive ratio |
|---|---|---|---|
| Tacrine | 1.57 | 0.65 | 0.41 |
| (1) | 23 | 34 | 1.47 |
| (2) | 43 | 39 | 0.90 |
| (3) | 62 | 102 | 1.65 |
| (4) | 31 | 73 | 2.40 |
| (5) | 22 | 30 | 1.36 |
| (6) | 43 | 70 | 1.63 |
| (7) | 72 | 128 | 1.78 |
| (8) | 29 | 61 | 2.08 |
| (9) | 737 | 1394 | 1.89 |
| (10) | 357 | 1189 | 3.34 |
| (11) | 3.5 | 4.5 | 1.27 |
| (12) | 3.5 | 3.4 | 0.96 |
| (13) | 2.9 | 7.1 | 2.40 |
| (14) | 11.1 | 9.6 | 0.87 |
| (15) | 8.7 | 8.7 | 1.00 |
| (16) | 8.6 | 17.1 | 1.99 |
| (17) | 8.5 | 15.7 | 1.85 |
| (18) | 4.8 | 10.1 | 2.10 |
| (19) | 3.4 | 1.9 | 0.58 |
| (20) | 15.5 | 12.1 | 0.78 |
| Propoxur | 6348 | 9 | 0.0014 |

2) Inhibitory Property with Regard to Extracts or Mosquito Larvae

Larvae of *Culex pipiens* mosquitoes which are sensitive or resistant to propoxur are milled in 400 µl of 0.25M phosphate buffer comprising 1% Triton X100. The homogenates are centrifuged at 10 000 rpm for 3 minutes.

The inhibition of the AChE1 activity is measured on the supernatant according to the method described in section 1), namely that 100 µl of supernatant are incubated for 15 minutes with 10 µl of compounds according to the invention at various concentrations. The activity of the known inhibitors of AChE, namely tacrine and propoxur, is also tested in parallel. The effectiveness of the various compounds with regard to the resistant larvae, relative to the sensitive larvae, is estimated by the sensitive/resistant ratio.

The results obtained ($IC_{50}$ in µM and sensitive/resistant ratio) are summarized below in table IV.

TABLE IV

| Compounds | Resistant larvae | Sensitive larvae | Sensitive/ resistant ratio |
|---|---|---|---|
| Tacrine | 5.5 | 3.5 | 0.6 |
| (1) | 6.2 | 29.4 | 4.7 |
| (2) | 28 | 442 | 15.5 |
| (3) | 33 | 118 | 3.5 |
| (4) | 7.5 | 74.3 | 9.8 |
| (5) | 81 | 592 | 7.3 |
| (6) | 27 | 330 | 12.0 |
| (7) | 21 | 132 | 6.1 |
| (8) | 51 | 91.6 | 1.8 |
| (11) | 14 | 111 | 7.7 |
| (12) | 6 | 54 | 8.5 |

TABLE IV-continued

| Compounds | Resistant larvae | Sensitive larvae | Sensitive/ resistant ratio |
|---|---|---|---|
| (13) | 89 | 236 | 2.7 |
| (14) | 142 | 2121 | 15.0 |
| (15) | 177 | 1220 | 6.9 |
| (16) | 22 | 490 | 22.5 |
| (17) | 35 | 424 | 12.2 |
| (18) | 37 | 260 | 7.1 |
| (19) | 19 | 312 | 16.7 |
| (20) | 152 | 153.0 | 1.0 |
| Propoxur | 31 820 | 4.9 | 0.00015 |

These combined results show that the compounds of formula (I) according to the invention are capable of effectively inhibiting the AChE activity and in particular the activity of a mutated AChE.

EXAMPLE 2

Insecticidal Property of the Compounds of the General Formula (I)

The insecticidal activity of the compounds according to the invention denoted in table IV below is tested on larvae of mosquitoes *Culex pipiens* sensitive or resistant to the action of propoxur.

The larvae resistant or sensitive to propoxur are incubated in 24-well plates, at the rate of 15 stage-4 larvae per well, in 1 ml of tap water comprising different concentrations of compounds ranging from 0.31 to 50 μg/ml.

Larval mortality is measured after incubating for 24 hours. For each compound, the dose resulting in 50% mortality ($LD_{50}$ in μM) is estimated using the log-Probit program (Raymond, M. (1985). Présentation d'un programme Basic d'analyse log-probit pour micro-ordinateur [Presentation of a Basic program for log-Probit analysis for a micro computer). Cahiers ORSTOM, série Entomologie médicale et Parasitologie, 23(2), 117-121; Raymond, M., Prato, G. and Ratsira, D. (1993). PROBIT, CNRS-UMII, Licence L93019. Avenix, 34680 St. Georges d'Orques, France.), the homogeneity of the dose/response being tested. The effectiveness of the different compounds with regard to the resistant larvae, relative to the sensitive larvae, is estimated by the sensitive/resistant ratio.

The results obtained ($LD_{50}$ in μM and sensitive/resistant ratio) are summarized below in the following table V.

TABLE V

| Compounds | Resistant larvae | Sensitive larvae | Sensitive/ resistant ratio |
|---|---|---|---|
| (1) | 143 | 310 | 2.2 |
| (2) | 170 | 455 | 2.7 |
| (3) | 122 | 389 | 3.2 |
| (4) | 200 | 576 | 2.9 |
| (5) | 206 | 300 | 1.5 |
| (6) | 192 | 762 | 4.0 |
| (8) | 123 | 223 | 1.8 |
| Propoxur | 2700 | 1.7 | 0.00063 |

These results clearly demonstrate that the compounds of formula (I) according to the invention are effective as insecticides and in particular with regard to populations of insects which are resistant to conventional insecticides of the propoxur type.

EXAMPLE 3

Preparation of an Insecticidal Composition According to the Invention 42 mg of the compound (I) are introduced into 100 ml of tap water and then the mixture is stirred.

What is claimed is:

1. A composition comprising at least one compound of general formula (I):

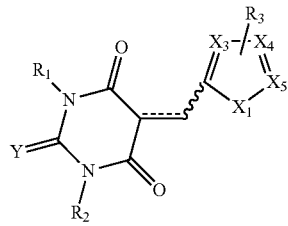

wherein:
- - - represents a bond which can be a single bond or a double bond;
$R_1$ represents a group selected from a hydrogen atom, a saturated or unsaturated, linear, branched or cyclic, $C_1$-$C_6$ alkyl group optionally substituted by a hydroxyl group or a halogen atom;
$R_2$ represents a group selected from an aryl group that is optionally substituted, a saturated or unsaturated, linear, branched or cyclic, $C_1$-$C_4$ alkyl group optionally substituted by one or more groups selected from a halogen atom, a hydroxyl group, and a heterocycle comprising 1 to 5 carbon atoms and 1 to 5 heteroatoms, wherein the heteroatoms are, individually, selected from oxygen, sulfur and nitrogen, and combinations thereof;
$R_3$ can be in a 3, 4 or 5 position of the ring and represents a group selected from a hydrogen atom and a saturated or unsaturated, linear, branched or cyclic, $C_1$-$C_4$ alkyl group optionally substituted by a hydroxyl group or a halogen atom;
$X_1$ represents an atom selected from sulfur, nitrogen and oxygen;
$X_3$, $X_4$ and $X_5$, which are identical or different, are selected from a carbon atom and a nitrogen atom, wherein at most two atoms from $X_3$, $X_4$ and $X_5$ are nitrogen atoms; and
Y represents an atom selected from oxygen and sulfur;
in combination with a carrier,
wherein the composition additionally comprises at least one other compound possessing an insecticidal activity selected from an organophosphorus compound, a carbamate, and combinations thereof.

2. A composition comprising at least one compound of general formula (I):

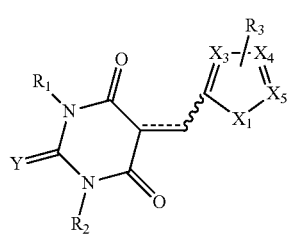

wherein:
- - - represents a bond which can be a single bond or a double bond;
$R_1$ represents a group selected from a hydrogen atom, a saturated or unsaturated, linear, branched or cyclic, $C_1$-$C_6$ alkyl group optionally substituted by a hydroxyl group or a halogen atom;
$R_2$ represents a group selected from an aryl group that is optionally substituted, a saturated or unsaturated, linear, branched or cyclic, $C_1$-$C_4$ alkyl group optionally substituted by one or more groups selected from a halogen atom, a hydroxyl group, and a heterocycle comprising 1 to 5 carbon atoms and 1 to 5 heteroatoms, wherein the heteroatoms are, individually, selected from oxygen, sulfur and nitrogen, and combinations thereof;
$R_3$ can be in a 3, 4 or 5 position of the ring and represents a group selected from a hydrogen atom and a saturated or unsaturated, linear, branched or cyclic, $C_1$-$C_4$ alkyl group optionally substituted by a hydroxyl group or a halogen atom;
$X_1$ represents an atom selected from sulfur, nitrogen and oxygen;
$X_3$, $X_4$ and $X_5$, which are identical or different, are selected from a carbon atom and a nitrogen atom, wherein at most two atoms from $X_3$, $X_4$ and $X_5$ are nitrogen atoms; and
Y represents an atom selected from oxygen and sulfur;
in combination with a carrier,
wherein the composition additionally comprises at least one other active substance selected from an acaricide, a fungicide, a bactericide, a manure, a fertilizer, and combinations thereof.

\* \* \* \* \*